United States Patent [19]

Abrahamson et al.

[11] Patent Number: 5,378,126

[45] Date of Patent: Jan. 3, 1995

[54] DIAPHRAGM CASSETTE FOR SOLUTION PUMPING SYSTEM

[75] Inventors: Kent D. Abrahamson; John E. Ogden, both of Libertyville, Ill.

[73] Assignee: Abbott Laboratories, Abbott Park, Ill.

[21] Appl. No.: 254,446

[22] Filed: Jun. 6, 1994

Related U.S. Application Data

[63] Continuation of Ser. No. 998,232, Dec. 30, 1992, abandoned.

[51] Int. Cl.⁶ .................................... F04B 43/02
[52] U.S. Cl. .................................... 417/479; 417/480; 417/413.1
[58] Field of Search ............ 417/360, 413 R, 479, 417/480; 604/113, 154

[56] References Cited

U.S. PATENT DOCUMENTS

| | | | |
|---|---|---|---|
| 4,276,004 | 6/1981 | Hahn | 417/479 |
| 4,303,376 | 12/1981 | Siekmann | 417/479 |
| 4,391,600 | 7/1983 | Archibald | 417/478 |
| 4,411,603 | 10/1983 | Kell | 604/153 |
| 4,657,490 | 4/1987 | Abbott | 417/478 |
| 4,758,238 | 7/1988 | Sundblom et al. | 604/153 |
| 4,818,186 | 4/1989 | Pastrone et al. | 417/413 R |
| 4,892,584 | 6/1989 | Pastrone | 604/153 |
| 5,056,992 | 10/1991 | Simons | 417/478 |
| 5,062,774 | 11/1991 | Kramer et al. | 417/413 |
| 5,098,262 | 3/1992 | Wecker et al. | 417/479 |

*Primary Examiner*—Louis J. Casaregola
*Assistant Examiner*—Peter Korytnyk

[57] ABSTRACT

A solution pumping system including a disposable pump cassette is disclosed, with the system configured for efficient and accurate preparation of parenteral admixture solutions. The system includes a pump driver having a reciprocable pump plunger and a plurality of associated valve actuators. The disposable pump cassette of the system is configured for removable positioning in operative association with the pump driver, and includes a positive displacement pump configured for operation by the reciprocable pump plunger. The pump cassette further includes a plurality of liquid inlets, and at least one liquid outlet joined in fluid communication with the inlets. By selective operation of the valve actuators of the pump driver, one or more selected source solutions are drawn through the pump inlets by the positive displacement pump, and directed through the pump outlet to an admixture solution container.

8 Claims, 3 Drawing Sheets

1

DIAPHRAGM CASSETTE FOR SOLUTION PUMPING SYSTEM

This application is a File-Wrapper-Continuation of U.S. application Ser. No. 07/998,232, filed Dec. 30, 1992, now abandoned.

FIELD OF THE INVENTION

The present invention generally relates to a solution pumping system for the preparation and administration of parenteral solutions, and more particularly to a solution pumping system including a disposable pump cassette having an elastomeric diaphragm configured for efficient and accurate compounding of parenteral solutions, and other solution pumping applications requiring delivery of multiple solutions to a common delivery point.

BACKGROUND OF THE INVENTION

Hospitals and other health care facilities prepare and administer on a daily basis a significant number of parenteral solutions. These parenteral solutions include both nutritional as well as drug-containing therapeutic solutions. Because of the large number of such solutions which must be handled on a daily basis in a health care facility, efficient and accurate preparation and administration of such solutions is necessary.

A significant advancement in recent years has been the development of positive displacement fluid infusion pumping devices for intravenous or intramuscular administration of solutions to patients. Pump systems have replaced gravity flow control systems, primarily due to the greater accuracy in delivery rates and dosages of pumps, and the relative sophistication of processor controlled pumps in permitting flexible and controlled feed from multiple liquid sources. In particular, such infusion pumping devices permit precise control of drug administration to a patient over a given period of time.

The LifeCare® 5000 Drug Delivery System is a positive displacement fluid infusion pump that is currently manufactured by Abbott Laboratories and is widely used in the patient care field. U.S. Pat. Nos. 4,639,245, to Pastrone et al., 4,818,186, to Pastrone et al., and 4,842,584, to Pastrone, all of which are hereby incorporated by reference, disclose the above positive displacement fluid infusion pumping device and related components. The LifeCare Drug Delivery System for infusion pumping includes a pump driver and an associated removable and disposable pump cassette. The pump cassette includes a self-contained positive displacement pump component, which is operated for fluid movement by a reciprocable pump plunger of the associated pump driver. The pump driver further includes selectively operable valve actuators which cooperate with valve mechanisms in the pump cassette.. The Life-Care Drug Delivery System thus provides accurate and highly automated administration and infusion of parenteral solution.

There is a need for a solution pumping system including a disposable pump cassette which will permit the same highly-desirable efficiency, accuracy, and automation in the compounding and preparation of such parenteral solutions. While the needed system is particularly suited for preparation of small volume parenteral solutions, typically including drugs or other therapeutic agents for administration to patients, the principles are equally suitable for a system for preparation of large volume parenterals, typically comprising nutritional solutions for patients, as well as for use with other applications requiring compounding of multiple reagents or therapeutic agents.

Currently small volume parenteral solutions typically are prepared manually. The pharmacist selects an intravenous solution container, typically a flexible bag, that is either partially empty, or that contains the appropriate base nutritional solutions or diluents. The pharmacist then calculates the amounts of the various liquid components that need to be added to the solution container in accordance with the physician's order. These components are then measured by drawing them into syringes of the appropriate sizes. The contents of the syringes are then injected into the final solution container.

Accurate preparation of parenteral solutions in this manner is time consuming, typically taking 20–30 minutes per physician order, assuming about 10 minutes of preparation time per bag when making three bags with six solution additions per bag. While appropriate protocols are established and followed for accuracy and consistency, the manual nature of the procedure does not preclude the possibility of errors in the preparation of the resultant admixtures. Additionally, the repeated needle-puncturing and additions of solutions to the admixture container increase the risk of contamination.

The solution pumping system of the present invention, including a disposable pump cassette, is particularly configured to facilitate accurate and efficient compounding of parenteral admixture solutions with minimal labor and a reduced risk of contamination.

SUMMARY OF THE INVENTION

The present solution pumping system, including a disposable pump cassette is particularly configured for efficient and accurate admixture of source solutions, particularly the preparation of small volume parenteral solutions. The system is arranged such that all source solutions and resultant admixtures flow through and only contact the disposable pump cassette and associated fluid handling tubing and containers. The pump cassette is further configured to enhance seal integrity and ease of use.

The present solution pumping system includes a pump driver and a removable and disposable pump cassette. The pump driver, which is preferably provided with suitable automatic and programmable controls, includes a pump driver in the form of a reciprocable pump plunger, and a plurality of valve actuators, which are preferably solenoid-operated. For compounding parenteral solutions, the pump driver is ordinarily positioned in the pharmacy of a health care facility, typically in a laminar flow hood to abate contamination.

The pump cassette of the present solution pumping system interfaces with the pump driver, and provides the actual pump and valve mechanisms which permit compounding of plural source solutions for preparation of parenteral admixture solutions. The pump cassette includes a rigid cassette body comprising a plate-like front body member and a juxtaposed plate-like rear body member. The cassette further includes a membrane-like elastomeric diaphragm positioned in the cassette body between the front and rear body members.

The cassette body and the diaphragm provide the pump cassette with a plurality of liquid inlets, at least one liquid outlet, and a liquid flow path for joining the liquid inlets and outlet in fluid communication. The diaphragm cooperates with the cassette body to provide a valve mechanism at each of the various inlets and at the outlet of the cassette. In the preferred embodiment illustrated herein, the front body member of the cassette body defines the liquid inlets, outlet, and flow path, together with the associated diaphragm. The rear body member cooperates with the diaphragm and the front body member to hold the diaphragm in sealing engagement with the front body member. The rear body member defines a plurality of openings for engagement of the diaphragm by the pump plunger, and for engagement of the valve actuators of the pump driver with the valve mechanisms of cassette.

The pump cassette further includes a positive displacement liquid pump chamber which is operatively driven by the pump plunger of the pump driver, and which pumps liquid from a selected one of the liquid inlets to the liquid outlet via the flow path of the cassette. In the preferred form, the pump chamber is defined by the front body portion of the cassette body and a portion of the cassette diaphragm juxtaposed to the cassette body.

Liquid flow is effected by reciprocation of the pump plunger against the diaphragm, in timed relation to operation of a selected upstream valve mechanism (such as at one of the liquid inlets) and a selected downstream valve mechanism (such as at the liquid outlet).

The pump cassette of the present invention enhances its sealing integrity. Formation of the cassette body from rigid thermoplastic resin facilitates joining of the body members by sonic welding. To this end, the front and rear body members of the cassette are joined to each other at a marginal joint extending along at least a portion of the confronting marginal edges of the body members. Notably, the front and rear body members are further joined together inwardly of the marginal joint at a diaphragm joint. The diaphragm joint extends completely about the periphery of the cassette diaphragm, thus enhancing the sealing of the liquid flow path of the cassette. By completely encapsulating and enclosing the diaphragm, the quantity of relatively expensive elastomer employed for molding the diaphragm is desirably decreased, since the diaphragm need not extend all the way to the confronting marginal edges of the front and rear body members.

The diaphragm of the cassette further includes a reinforced portion for abutment with the plunger and an unreinforced portion surrounding the reinforced portion. This feature improves the life of the diaphragm for pumps that have high cycles, such as for example compounding pumps by removing the stress points from contact with the piston plunger.

Numerous other features and advantages of the present invention will become readily apparent from the following detailed description, the accompanying drawings, and the appended claims.

DETAILED DESCRIPTION

Figure 1:
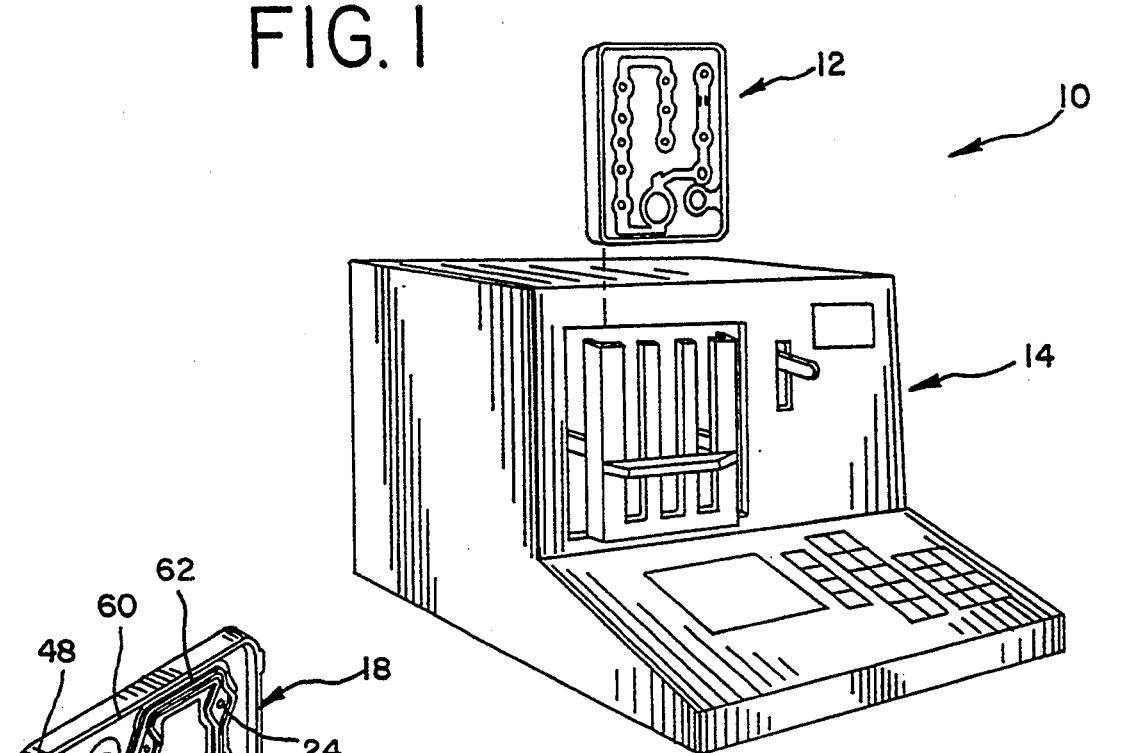
FIG. 1 is a perspective view of a solution pumping system, including a pump driver and a disposable pump cassette, which is operable in accordance with the principles of the present invention.

While the present invention is susceptible of embodiment in various forms, there is shown in the drawings and will hereinafter be described a presently preferred embodiment of the invention, with the understanding that the present disclosure is to be considered an example of the invention, and is not intended to limit the invention to the specific embodiment illustrated.

With reference now to the drawings, therein is illustrated a solution pumping system embodying the principles of the present invention. In the illustrated embodiment, the present system has been particularly configured for compounding of parenteral admixture solutions for intravenous or intramuscular administration to patients. For use in this manner, the present compounding system is supplied through tubing with a plurality of source solutions from associated containers. The source solutions are compounded, in accordance with a physician's order, to form an admixture solution in an admixture container for subsequent patient administration. However, the solution pumping system, including a disposable pump cassette, embodying the principles of the present invention can be used for other solution pumping applications when it is desirable to deliver a plurality of different source solutions to a single delivery point such as a container or patient catheter, for example.

Referring now to FIG. 1, the pumping system 10 of the present invention includes a disposable pump cassette 12 which is driven by, and can be removably received within, a pump driver 14. As will be further described, the pump cassette 12, together with its associated tubing (typically referred to as a "transfer set") are disposable and are the only portions of the present system which contact the various source solutions and resultant admixtures. Thus, the pump cassette and tubing are intended for periodic disposal, such as on a daily basis.

Figure 2:
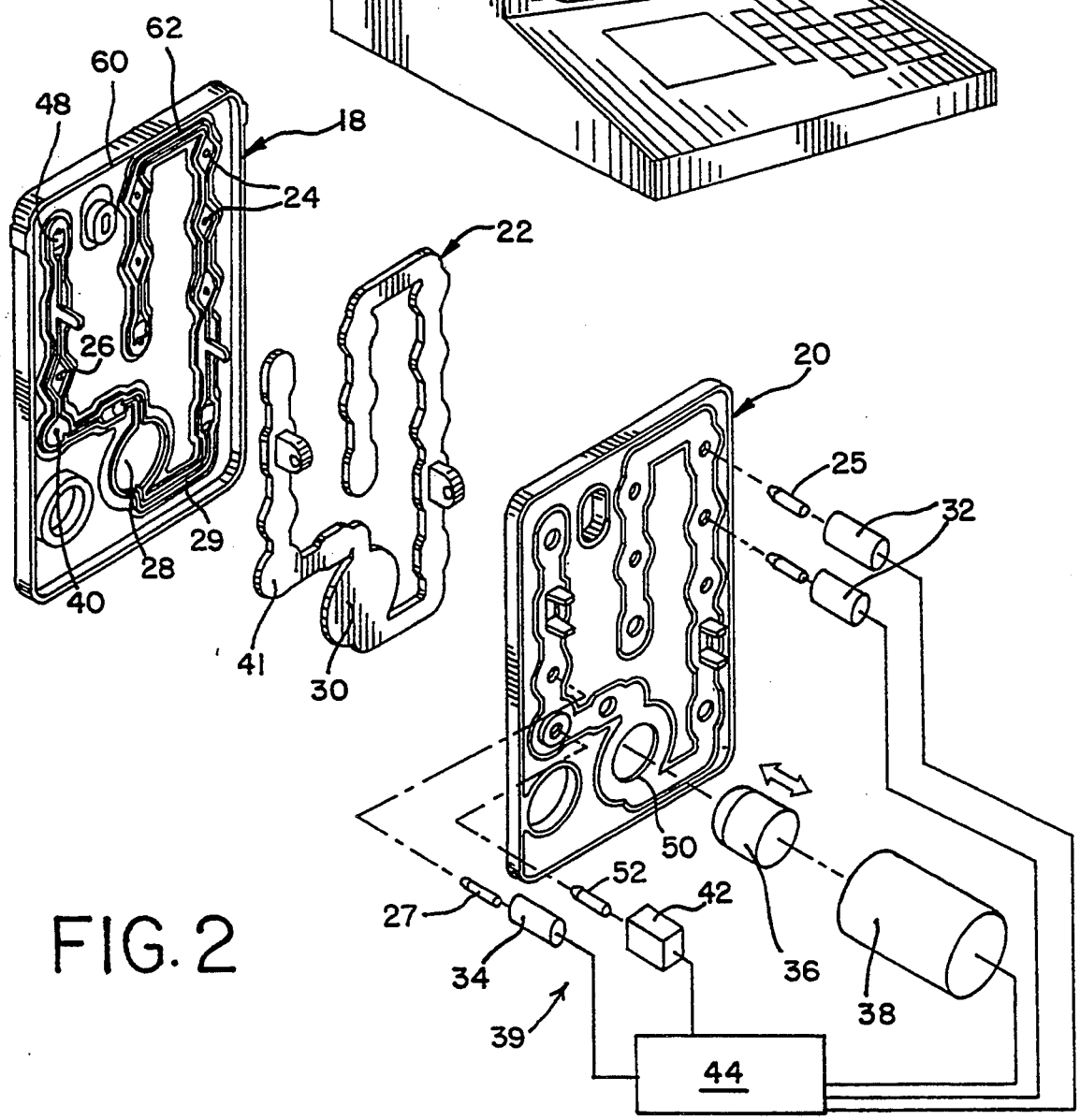
FIG. 2 is a diagrammatic, exploded perspective view illustrating the construction of the pump cassette shown in FIG. 1, and the manner in which the components of the associated pump driver cooperate with the pump cassette.
Figure 3:
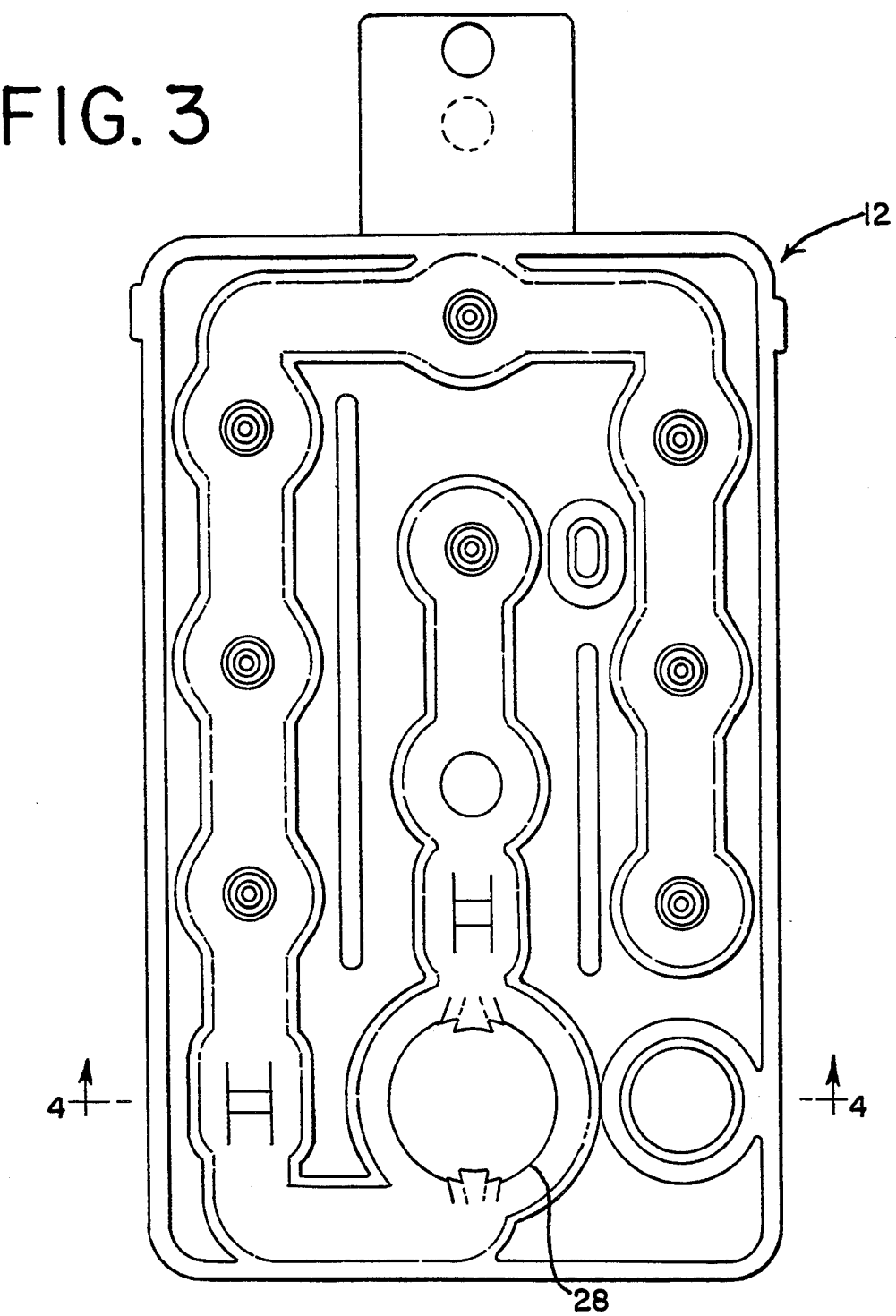
FIG. 3 is a plan view of a preferred embodiment of a disposable pump cassette.
Figure 4:
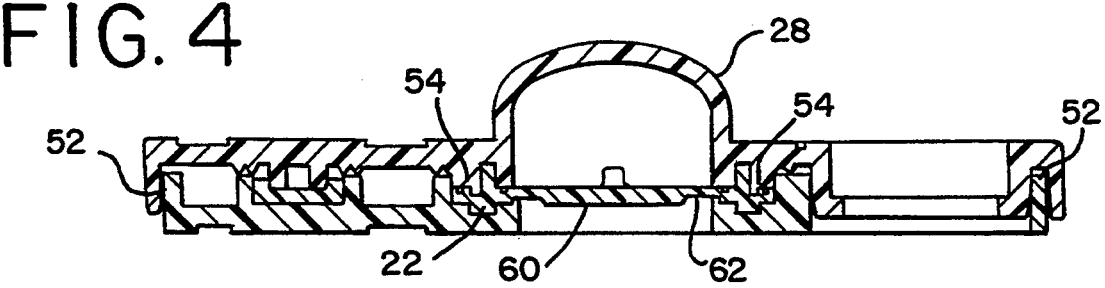
FIG. 4 is a cross sectional view along the line 4—4 of the pump cassette of FIG. 3 showing the cassette diaphragm of the pumping chamber according to the present invention.
Figure 5:
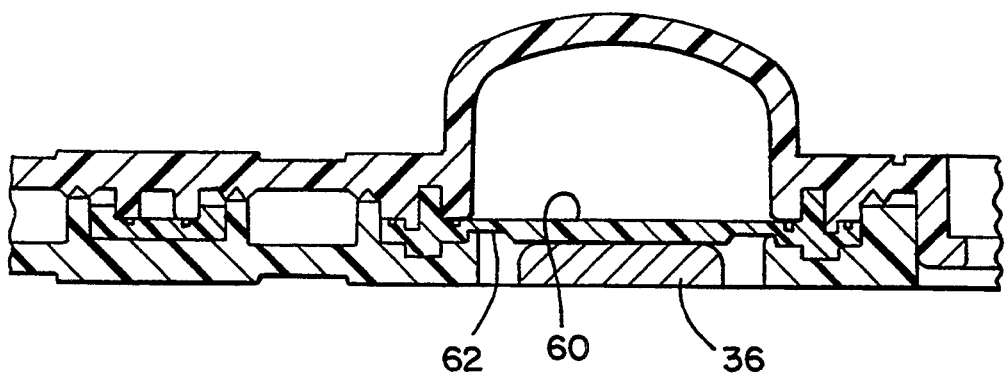
FIG. 5 is an enlarged section view of FIG. 4 showing the pump piston in the retracted position and the cassette diaphragm in the initial prestressed position.

The present pump cassette is configured to facilitate its efficient manufacture, but at the same time includes a number of structural features which lend to accurate, efficient, and reliable use of the present system. As shown in FIG. 2, the pump cassette comprises a rigid, generally rectangular cassette body 12 which comprises a front body member 18 and a juxtaposed rear body member 20. The cassette body is preferably formed from rigid thermoplastic material, such as polycarbonate.

The pump cassette further includes a deformable elastomeric diaphragm 22 positioned between the front and rear body members. Diaphragm 22 cooperates with the cassette body 12, and in particular the front body member 18, to define and provide a plurality of liquid inlets 24, at least one liquid outlet 26, and a liquid flow path 29 joining the inlets and outlet in fluid communication. The diaphragm cooperates with the front body member 18 to provide a selectively operable inlet valve mechanism 25 at each of the various liquid inlets and selectively operable outlet valve mechanism 27 at the liquid outlet.

The diaphragm 22 also cooperates with the front body member 18 of the cassette body to provide a positive displacement liquid pump 32 for pumping liquid from a selected one of the liquid inlets to the liquid outlet via the liquid flow path, as will be further described.

In order to ensure the integrity of the pump cassette construction, the plate-like front and rear body members 18 and 20 are preferably joined to each other in a substantially permanent manner. A marginal joint seal 52 is provided which extends along at least a portion of the confronting marginal edges of the body members.

Notably, the front and rear body members are further preferably joined to each other at a diaphragm joint seal 54 which extends continuously and completely about the entire periphery of the cassette diaphragm where rear body member wall portions abut the front body member.

In keeping with the fundamental concept of the present system that all liquid flow through the system is only through the pump cassette 12, the pump cassette further includes a positive displacement liquid pump component 31. The pump component includes a pump chamber 28 which is defined by front body member 18 of the cassette body, and further includes a confronting portion 30 of the diaphragm 22, which cooperates with the pump chamber 28 for effecting flow of liquid within the flow path of the pump cassette. This is achieved by deformation and relaxation of the diaphragm portion 30 by a reciprocable pump plunger 36 of the associated pump driver 14. The pump plunger 36 acts against the diaphragm portion 30 through a plunger opening 50 defined by rear body member 20.

Figure 6:
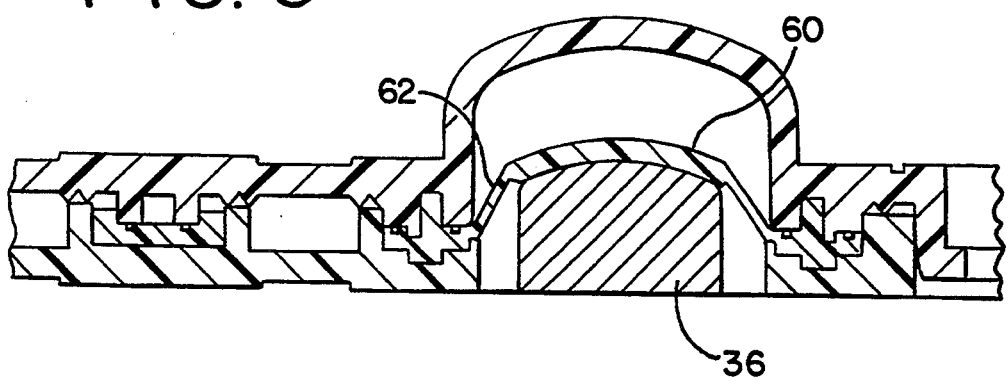
FIG. 6 is an enlarged section similar to FIG. 5 showing the pump piston in the home position and the cassette diaphragm in the neutral position.
Figure 7:
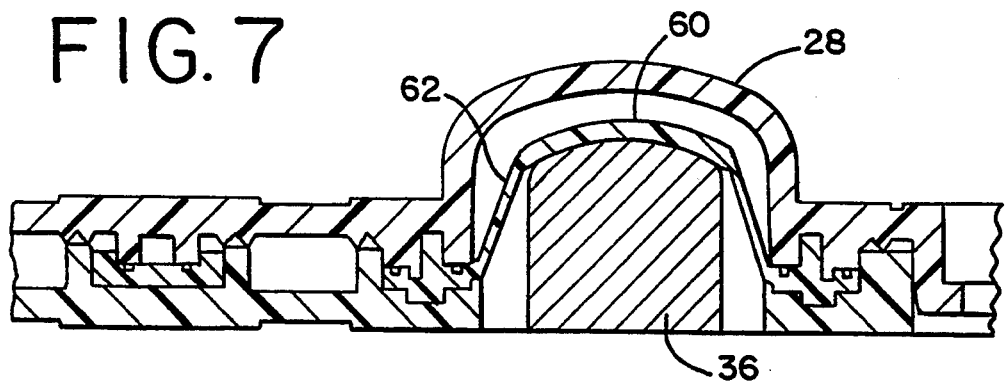
FIG. 7 is an enlarged section similar to FIG. 5 showing the pump piston in the fully extended position and the cassette diaphragm in the stretched position.

Operation of the pump is in accordance with U.S. Pat. No. 4,639,245, to Pastrone et al., the disclosure of which is hereby incorporated by reference. Essentially, liquid flow is effected by reciprocation of pump plunger 36 in timed relation to operation of inlet and outlet actuators 32 and 34. A reversible stepping motor 38, acting through a suitable threaded connection, provides reciprocable stroking of the pump plunger for alternately deforming on stretching the diaphragm portion 30 as shown in FIG. 7 for example, and relaxing the diaphragm portion 30 as shown in FIG. 6 for example, thus effecting positive displacement of liquid in the pump chamber 28. During extension of the plunger, for effecting positive liquid flow, outlet actuator 34 is retracted so as to open the liquid outlet 26, while the selected inlet actuator 37 closes the selected liquid inlet 24, Conversely, the liquid outlet 26 is closed, and the selected liquid inlet 24 is opened during retraction of the pump plunger 36, whereby retraction of the pump diaphragm portion 30 effects filling of the pump chamber via the liquid inlet and the flow path 29.

As will be appreciated, the pump component can readily be reversibly operated to provide reverse liquid flow in flow path 29. This merely entails reversing the above-described operation of the selected upstream and downstream valve mechanisms so liquid flows in a reverse direction through the pump. As will be further described, this technique is employed for effecting reverse fluid flushing in the cassette by introduction of flush liquid into a flush fluid inlet 48 downstream of outlet 26.

Because the pump chamber 28 and pump diaphragm portion 46 together define a predetermined volume and maximum possible displacement for the liquid pump 31, precise control of pump plunger 36 permits precise control of liquid flow through the cassette, thus particularly facilitating accurate and consistent preparation of parenteral solutions. To this end, the pump cassette has been particularly configured to maintain consistent displacement for the pump 31, and to assure consistency of operation from one disposable pump cassette 12 to another.

As best seen in FIGS. 4–7, the diaphragm of the cassette further includes a reinforced portion for abutment with the plunger 36 and an unreinforced portion 62 surrounding the reinforced portion. This feature improves the life of the diaphragm 22 for pumps that operate at high cycles, such as compounding pumps, by removing the stress points from contact with the piston plunger.

From the foregoing, it will be observed that numerous modifications and variations can be effected without departing from the true spirit and scope of the novel concept of the present invention. It is to be by the appended claims all such modifications as fall within the scope of the claims.

What is claimed is:

1. A pump cassette for use with a related pump driver having a reciprocable pump plunger and a plurality of valve actuators, the pump plunger having a face surface, said pump cassette comprising:
    a rigid cassette body having a front body member and a rear body member;
    a plurality of liquid inlets and at least one liquid outlet provided in the cassette body;
    a liquid flow path for joining said liquid inlets and at least one liquid outlet in fluid communication; and
    an elastomeric diaphragm positioned between the front and rear body member in said cassette body, the diaphragm including a diaphragm pumping portion operably associated with the pump plunger of said related pump driver for pumping liquid through the flow path from a selected one of said liquid inlets to said at least one liquid outlet, the diaphragm pumping portion including a reinforced diaphragm portion for contacting the face surface of the plunger and having a surface size equal or greater than the size of the face surface of the associated plunger and an unreinforced diaphragm portion surrounding the reinforced portion so that the unreinforced diaphragm portion is not in contact with the face surface of the plunger, the unreinforced diaphragm portion for stretching and relaxing in response to the reciprocation of the pump plunger.

2. The pump cassette of claim 1 further including:
    pinch means for circumferentially securing the diaphragm against radial movement within the cassette;
    first sealing means for fluidly isolating the diaphragm within the pumping chamber of the cassette;
    a reservoir portion to facilitate radial deformation within the cassette; and second substantially circumferential sealing means for further isolating the diaphragm within the pumping cassette.

3. An elastomeric diaphragm in a pump cassette for use with an associated pump driver having a reciprocable pump plunger, the pump plunger having a face surface, said elastomeric diaphragm comprising:

a reinforced diaphragm portion for abutting association with the face surface of the plunger, said reinforced portion having a size equal or greater than the size of the face surface of the associated plunger;

an unreinforced diaphragm portion surrounding the reinforced portion that is not in contact with the face surface of the plunger, the unreinforced diaphragm portion for stretching and relaxing in response to the reciprocation of the pump plunger;

pinch means for circumferentially securing the diaphragm against radial movement within the cassette;

first sealing means for fluidly isolating the diaphragm within the pumping chamber of the cassette;

a reservoir portion to facilitate radial deformation within the cassette; and second substantially circumferential sealing means for further isolating the diaphragm within the pumping cassette.

4. An elastomeric diaphragm in a pump cassette for use with an associated reciprocable pump plunger, the pump plunger having a face surface, said elastomeric diaphragm comprising:

a reinforced diaphragm portion for abutting association with the face surface of the plunger, said reinforced portion having a surface area at least the size of the face surface of the associated plunger; and an unreinforced diaphragm portion surrounding the reinforced diaphragm portion that is not in contact with the face surface of the plunger, the unreinforced diaphragm portion for stretching and relaxing in response to the reciprocation of the pump plunger.

5. The elastomeric diaphragm of claim 4 further comprising:

pinch means for circumferentially securing the diaphragm against radial movement within the cassette;

first sealing means for fluidly isolating the diaphragm within the pumping chamber of the cassette;

a reservoir portion to facilitate radial deformation within the cassette; and second substantially circumferential sealing means for further isolating the diaphragm within the pumping cassette.

6. The diaphragm of claim 4 for use in a rigid cassette body wherein the associated pump plunger operates with high cycle frequency for extended time periods.

7. The diaphragm of claim 6 wherein the reinforced portion is on the surface of the diaphragm that is opposite the surface in abutment with the plunger.

8. The diaphragm of claim 7 wherein the transition from reinforced to unreinforced includes a tapered transition.

* * * * *